United States Patent
Sarhan et al.

(10) Patent No.: US 10,709,616 B2
(45) Date of Patent: Jul. 14, 2020

(54) CONTACTLESS MAGNETIC PROBE SENSING AND IMPEDANCE IMAGING OF LIQUID AND SOLID EXCREMENT IN DIAPERS AND OTHER UNDERCLOTHING

(71) Applicants: Sameh Sarhan, Santa Clara, CA (US); Lawrence Herbert Zuckerman, Livermore, CA (US); Jihad Naja, San Jose, CA (US)

(72) Inventors: Sameh Sarhan, Santa Clara, CA (US); Lawrence Herbert Zuckerman, Livermore, CA (US); Jihad Naja, San Jose, CA (US)

(73) Assignee: Xtrava Inc., Santa Clara, CA (US)

( * ) Notice: Subject to any disclaimer, the term of this patent is extended or adjusted under 35 U.S.C. 154(b) by 0 days.

(21) Appl. No.: 15/589,672

(22) Filed: May 8, 2017

(65) Prior Publication Data
US 2018/0000659 A1    Jan. 4, 2018

Related U.S. Application Data
(60) Provisional application No. 62/333,855, filed on May 10, 2016.

(51) Int. Cl.
| | | |
|---|---|---|
| G08B 23/00 | (2006.01) | |
| A61F 13/42 | (2006.01) | |
| A61F 5/48 | (2006.01) | |
| G08B 21/04 | (2006.01) | |
| A61F 13/84 | (2006.01) | |

(52) U.S. Cl.
CPC .............. *A61F 13/42* (2013.01); *A61F 5/48* (2013.01); *G08B 21/0438* (2013.01); *A61F 2013/8479* (2013.01); *A61F 2013/8497* (2013.01)

(58) Field of Classification Search
None
See application file for complete search history.

(56) References Cited

U.S. PATENT DOCUMENTS

| | | | | | |
|---|---|---|---|---|---|
| 4,125,021 | A * | 11/1978 | Kamei | .................... | G01F 23/26 336/75 |
| 5,463,377 | A * | 10/1995 | Kronberg | .............. | G01M 3/045 340/592 |
| 5,469,146 | A * | 11/1995 | Gurler | .................... | A61F 13/42 128/886 |
| 8,471,715 | B2 * | 6/2013 | Solazzo | .................. | A61F 13/42 200/61.04 |
| 2003/0058901 | A1 * | 3/2003 | Jacobowitz | ............... | H01S 5/14 372/20 |
| 2004/0230172 | A1 * | 11/2004 | Shapira | .................... | A61F 13/42 604/361 |
| 2010/0168702 | A1 * | 7/2010 | Ales, III | ................. | A61F 13/42 604/361 |
| 2010/0262136 | A1 * | 10/2010 | Morgan | ................. | A61B 18/14 606/33 |
| 2011/0087308 | A1 * | 4/2011 | Morgan | .................. | A61N 1/06 607/63 |

(Continued)

*Primary Examiner* — Julie B Lieu (57) ABSTRACT

A system, apparatus, and method for detecting the presence and amount of liquid and/or solid excrement in diapers or other undergarments, using a miniature ultra-low power near-field electromagnetic probe, applicable circuitry, and additional sensor types, that is hand-held or attached to the outside of said garments

3 Claims, 6 Drawing Sheets

(56) References Cited

U.S. PATENT DOCUMENTS

| | | | | |
|---|---|---|---|---|
| 2011/0313260 | A1* | 12/2011 | Jeong | A61B 5/01 |
| | | | | 600/301 |
| 2014/0191768 | A1* | 7/2014 | Engl | G01R 35/005 |
| | | | | 324/601 |
| 2014/0200538 | A1* | 7/2014 | Euliano | A61F 13/42 |
| | | | | 604/361 |
| 2015/0080819 | A1* | 3/2015 | Charna | A61F 13/42 |
| | | | | 604/361 |
| 2015/0223755 | A1* | 8/2015 | Abir | A61F 13/42 |
| | | | | 600/300 |
| 2016/0043775 | A1* | 2/2016 | Ravani | G06K 19/0727 |
| | | | | 455/41.1 |
| 2016/0047932 | A1* | 2/2016 | Akaba | G01N 29/2443 |
| | | | | 324/727 |
| 2017/0035625 | A1* | 2/2017 | LaVon | A61F 13/49015 |
| 2017/0048651 | A1* | 2/2017 | Lin Charna | H04B 1/3888 |
| 2018/0000563 | A1* | 1/2018 | Shanjani | H04B 5/0056 |
| 2018/0221795 | A1* | 8/2018 | Bonifas | B01D 35/143 |
| 2018/0221796 | A1* | 8/2018 | Bonifas | C02F 1/485 |
| 2018/0263827 | A1* | 9/2018 | Omori | A61F 13/42 |
| 2018/0325743 | A1* | 11/2018 | Ho | A61F 13/42 |

\* cited by examiner

CONTACTLESS MAGNETIC PROBE SENSING AND IMPEDANCE IMAGING OF LIQUID AND SOLID EXCREMENT IN DIAPERS AND OTHER UNDERCLOTHING

CROSS-REFERENCE TO RELATED APPLICATION

Priority is claimed under 37 CFR 1.78 and 35 USC 119(e) to U.S. Provisional Application 62/333,855 (XT1605101), filed 10 May 2016), which is incorporated by reference.

TECHNICAL FIELD

This disclosure relates generally to instrumentation utilizing incident and reflective coupling of low frequency static magnetic fields to obtain data related to the composition, location, orientation, and motion of nearby electrically conducting objects. More specifically, this disclosure relates to the use of a magnetic coupling probe or probes, supplemented by additional sensors and related circuitry, located either in handheld instruments or miniature appliances attached to the outside of diapers or other clothing, to sense the presence of liquid and solid excrement discharged from infants, other infirm humans, and certain domesticated animals.

BACKGROUND

In all human cultures where infants, babies, and toddlers wear clothing, the issue of determining when underclothing such as diapers need to be changed represents a continuous nuisance, medical risk, expense, and waste of time. A similar issue exists for infirm adults, especially those who cannot communicate.

Often, babies are aroused from sleep unnecessarily to check a diaper, causing harm to them and disruption to caregivers. During automotive travel, it may be necessary to pull over and stop the vehicle in what may be unsafe or inclement conditions, just to determine whether a diaper needs to be changed. If a diaper is checked too late, the consequences could be painful and dangerous chafing and/or infiltration to other clothing and surrounding objects. The diaper wetness monitoring task is magnified when there are multiple babies or infirm patients.

Many sensing methods that automatically provide an alarm when a diaper has become wet have been advanced during the past twenty years or so. All of them require special diaper construction and/or devices that mount inside the diaper or other undergarment and make physical contact with excrement. Moreover, they are sensitive only to liquid waste.

In contrast, the methods described in the instant disclosure are sensitive to liquid and solid waste. They require no special clothing construction and employ only miniature electronic devices that are either hand held or attached to the outside of a diaper or other undergarment. The single device can be used repeatedly for a period of years with no maintenance, and it could include communication with the caregiver via wireless means. Moreover, the device itself and method of attachment to clothing are intrinsically safe for infants and babies.

BRIEF SUMMARY

This Brief Summary is provided as a general introduction to the Disclosure provided by the Detailed Description and Figures, summarizing some aspects of the disclosed invention. It is not a detailed overview of the Disclosure, and should not be interpreted as identifying key elements of the invention, or otherwise characterizing the scope of the invention disclosed in this Patent Document.

Reference is made to USPTO Application Number 15082638, filed 28 Mar. 2016, which is itself cross referenced to U.S. Provisional Application 62/141,272 filed 1 Apr. 2015). This application mentions the sensing of diaper wetness in paragraph 0056 and contains technical details to further support the instant application, which applies the methods therein specifically to a sensor of excrement present in undergarments. These patent applications are incorporated to the instant application by reference.

The contactless instrument that is either handheld or attached to the outside of a garment detects the presence of excrement in an undergarment such as a diaper and can distinguish between liquid and solid waste matter. This instrument uses the fact that the undergarment becomes electrically conductive or more conductive in the presence of liquid waste. It also uses the fact that solid waste is also electrically conductive. This instrument is also capable of distinguishing between electrical conductance of the undergarment and its contents, and that of the internal body tissue by varying penetration depth of the probe-generated excitation field. Finally, measurement reliability is improved through the use of additional sensors within the same instrument, such as temperature and acceleration.

Other aspects, features and advantages of the invention will be apparent to those skilled in the art from the following Disclosure.

BRIEF DESCRIPTION OF DRAWINGS

For a more complete understanding of this disclosure and its features, reference is now made to the following description, taken in conjunction with the accompanying drawings, in which.

DETAILED DESCRIPTION

The various figures, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

In general, this disclosure describes a technique for detecting liquid and solid excrement in undergarments such as a diaper, using an indefinitely re-usable instrument that makes no electrical contact with said undergarments and no contact at all with the inside of said undergarment.

Depending upon the implementation, this technique can provide significant benefits in a range of fields, such as the care of infants, babies, toddlers, infirm humans of all ages, domesticated primates and other animals.

Figure 1:
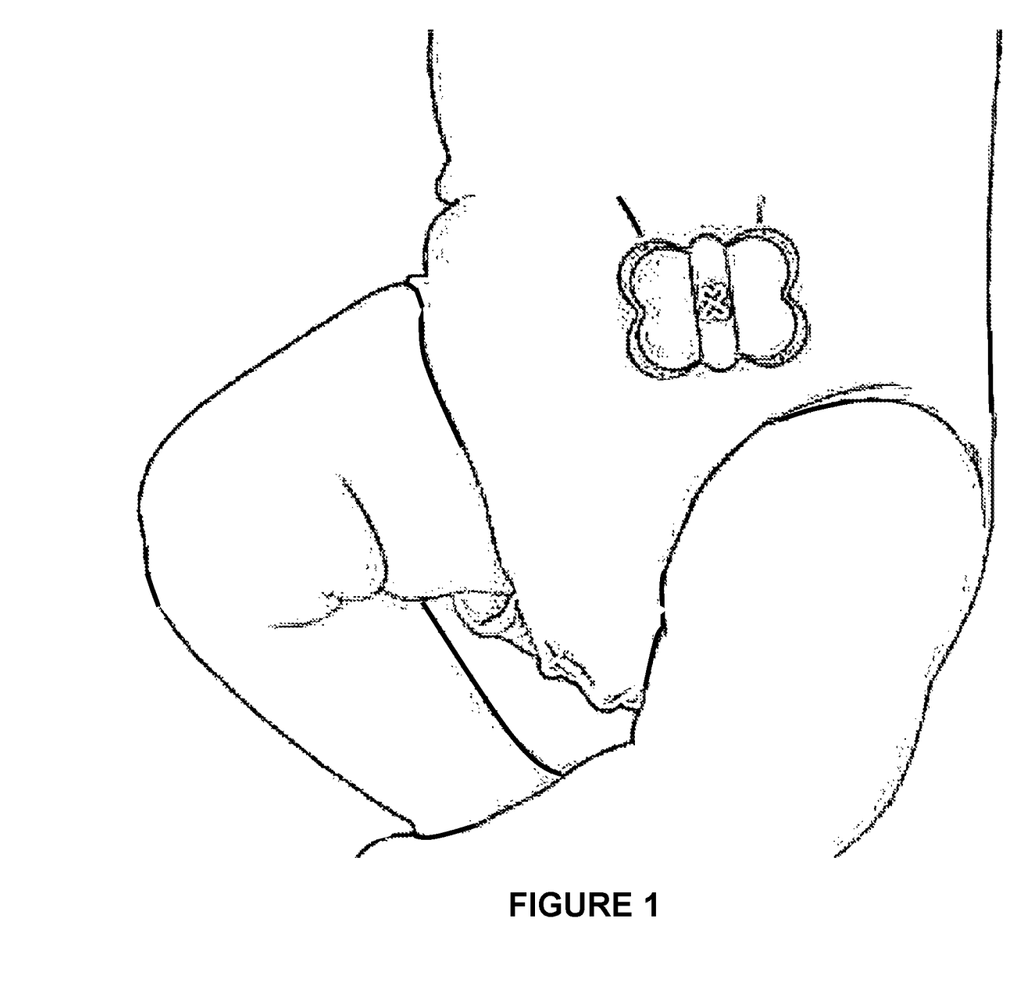
FIG. 1 shows an example instrument apparatus attached to the outside of a diaper being worn by a subject infant.
Figure 2:
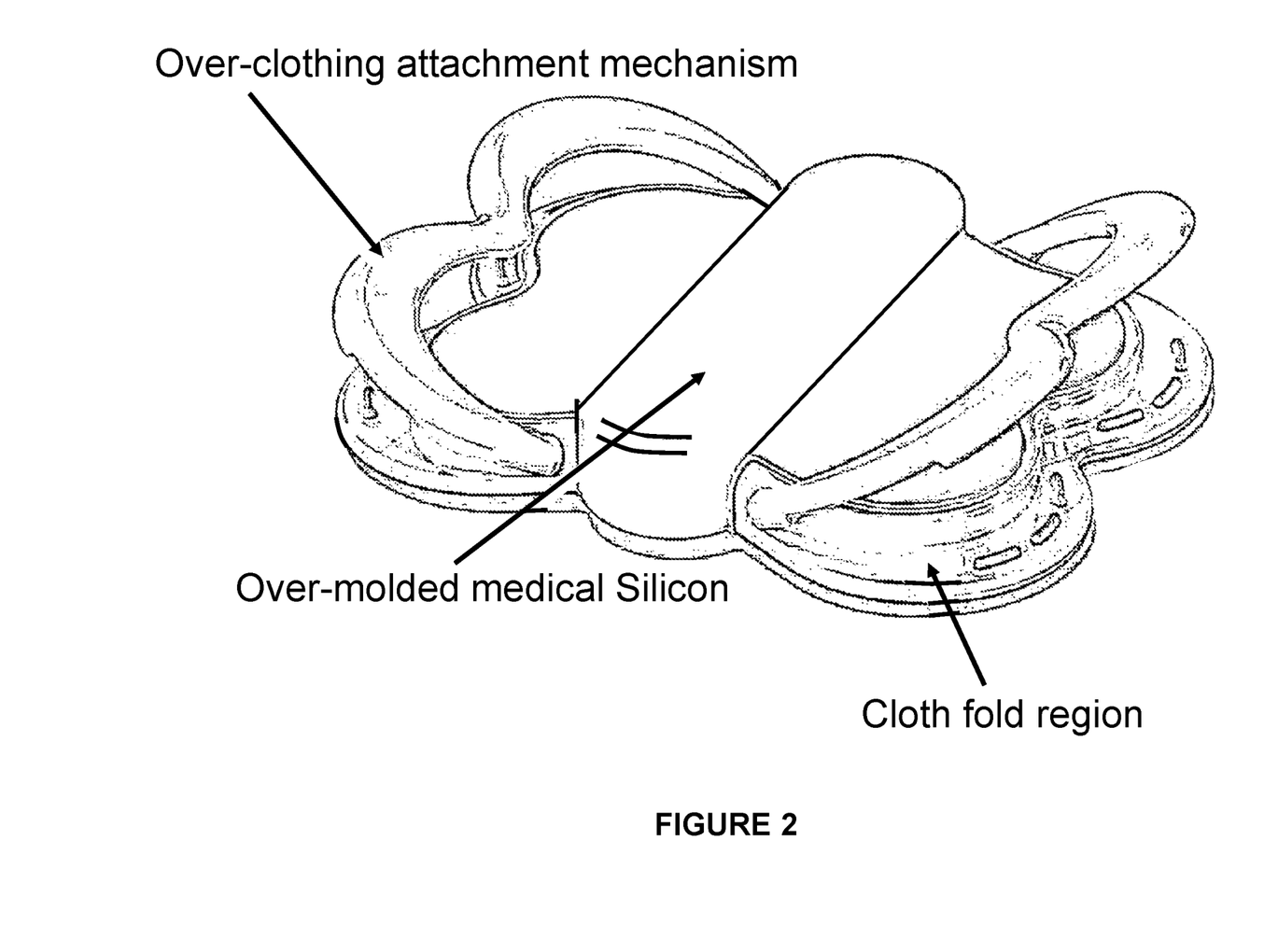
FIG. 2 shows another example instrument apparatus, with some construction detail.

FIG. 1 shows a photograph of a Subject infant wearing a diaper and additional garment. Attached to the additional garment is a butterfly-shaped appliance that contains wireless communication apparatus and various sensors, including a magnetic probe and applicable circuitry that detects, among other things, liquid and solid excrement present in said diaper. FIG. 2 shows some detail of the intrinsically safe butterfly-shaped appliance, including the over-clothing attachment means.

The example magnetic probe consists of a very high Q inductor coil in a parallel tuned circuit excited with a current at its resonant frequency. This current produces a tiny magnetic induction field, a portion of which exists within the diaper, which in turn induces a tiny electric current to flow in the diaper. The amplitude of this induced current depends upon the conductance of the diaper material and is related to the amount of liquid excrement present. The induced current amplitude also depends upon the quantity of solid excrement, also an electrical conductor, present therein. Said conductance is extremely low or zero when no excrement is present but increases to finite values, depending upon physical characteristics and quantity of same. As the conductance increases, the induced current also increases.

As the amplitude of induced current present within the diaper increases, its own magnetic induction field increases. A portion of this secondary magnetic field exists within the probe inductor coil. It can be shown that this secondary field induces a current in the probe inductor that is essentially opposite in phase to that of the original current, thus reducing the net current in this inductor. Therefore, measurement of probe tuned circuit current using circuitry within the appliance provides an indication of excrement level within the diaper.

Figure 3:
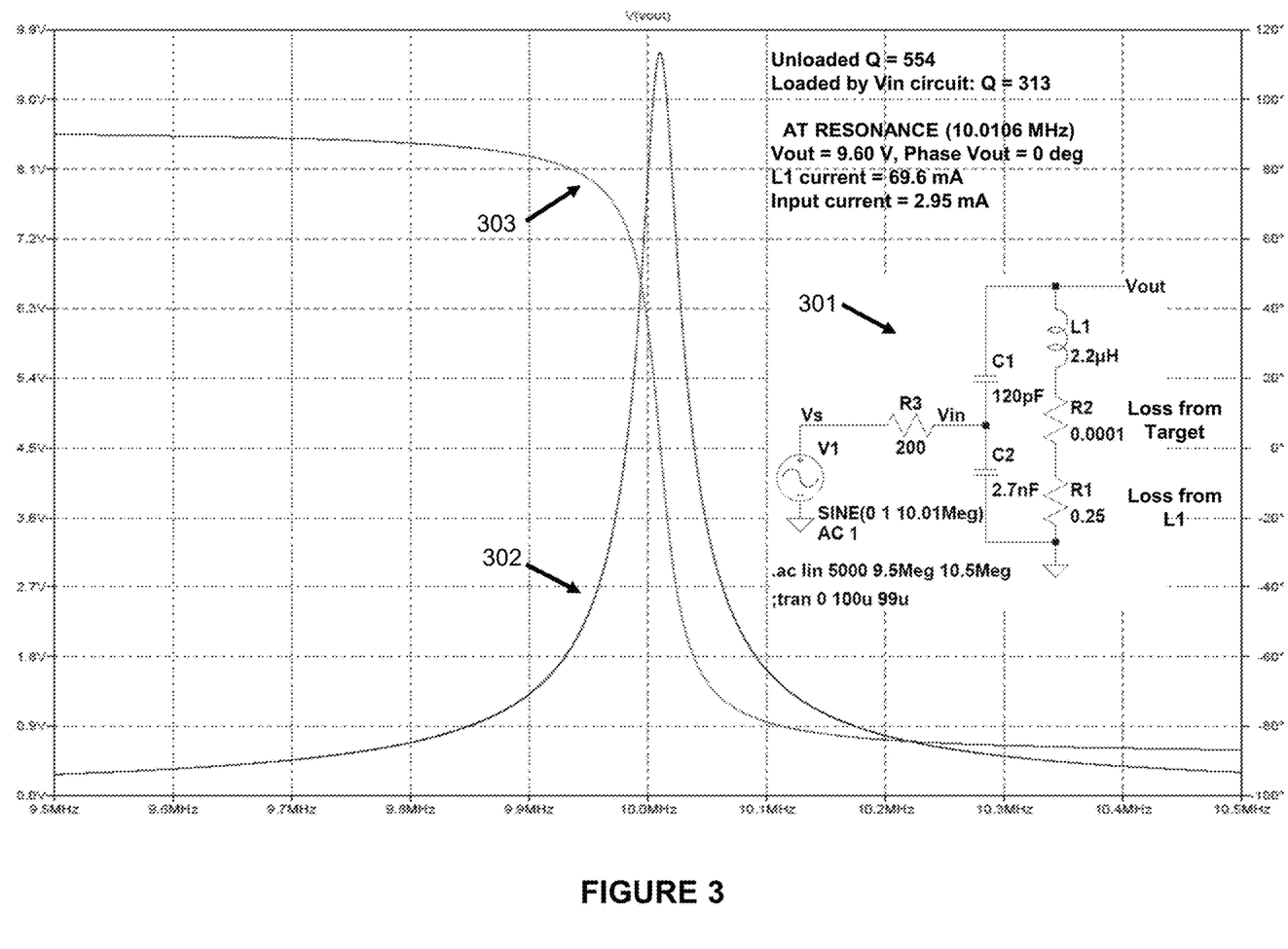
FIG. 3 shows the amplitude and phase response of a physically isolated parallel tuned circuit probe fed by a variable frequency generator.

FIG. 3 shows an example circuit 301 that may be used in said magnetic probe. L1 represents the probe inductor, placed within a parallel tuned circuit that also contains the real components, capacitors C1 and C2. In this example, the real component values cause the tuned circuit to be resonant at about 10 MHz. Thus, when the carrier signal source V1 is maintained at a constant voltage and is feeding power through R3 at this frequency, the current circulating around the tuned circuit 301 is at its peak, and so is the output voltage Vout.

Also present in tuned circuit 301 as drawn are two fictitious resistor components that represent losses to this circuit. R1 represents the losses of the real components—L1, C1, C2 and R3—losses within the tuned circuit or directly connected to it. These losses limit the circulating current and output voltage Vout. R2 represents losses from currents induced by L1 in nearby conducting objects whose secondary magnetic fields exist within L1, and also reduce the circulating current in tuned circuit 301. R2 is shown as essentially zero resistance, because probe tuned circuit 301 is intended to represent the case for which the diaper is free of all excrement and therefore presents zero conductivity. As no currents are induced by the magnetic induction field of L1, there are no secondary fields to affect the circulating current and output voltage Vout of tuned circuit 301.

Curve 302 shows how Vout varies with V1 frequency, assuming V1 voltage is maintained at 1 Volt. Curve 303 shows the phase angle difference between the signals at Vout and Vs. This phase angle is zero degrees at the resonant frequency. As the phase angle has opposite polarity when carrier source V1 is above and below tuned circuit 301 resonance, operation of an automatic control system to match tuned circuit frequency is facilitated. At resonance, the circulating current=69.6 mA, and Vout=9.60 Volts.

Figure 4:
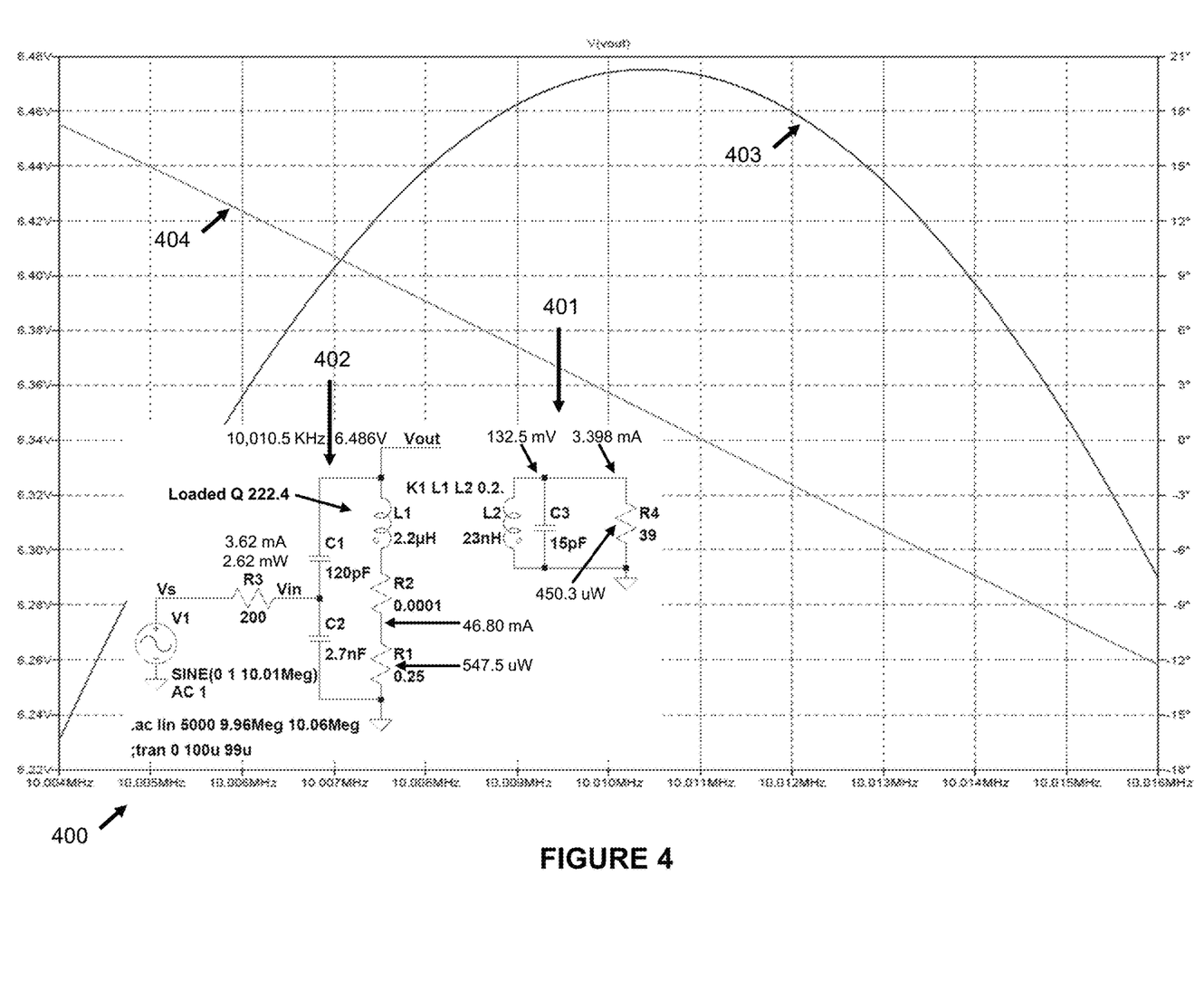
FIG. 4 shows the amplitude and phase response of the same parallel tuned circuit and variable frequency generator, but here the probe is in proximity with a body or object that provides a load, i.e. has a current induced by the currents flowing in the probe.

FIG. 4, shows the same probe tuned circuit as 402, with probe inductor L1 as shown in FIG. 3. For this case, however, the example diaper conditions including the presence of excrement are represented by the simulated circuitry 401. It is clear that current will flow through L2, C3, and R4. The magnetic fields from L1 and L2 that mutually penetrate are represented by a coupling constant K1=0.2. Under these conditions, at resonance, the tuned circuit 402 circulating current has been reduced to 46.8 mA, and the Vout has been reduced to 6.486 Volts.

Notice that curve 403 is much more broad than curve 303, and that curve 404 at zero degrees phase shift still locates the frequency of peak Vout with excellent accuracy. It should also be mentioned that if the materials within the diaper cause a significant phase shift, such a shift will be reflected to the probe tuned circuit, which will cause its resonant frequency to shift. Such a shift, if significant, could also be used to identify the presence of excrement and/or assist in its identification.

It should be understood that Circuit 401 also represents currents within the Subject's body; as a fraction of the magnetic fields from probe circuit 402 are present there in addition to within the diaper. Notice that the power dissipated the diaper, excrement, and Subject's body is less than 0.5 micro-Watt. This is about 5% of the universally accepted safe value for dissipation inside a human body.

The embodiment shown in FIGS. 3 and 4 show an example of how to detect the presence and amount of excrement in a diaper by monitoring the resonant frequency of a probe parallel tuned circuit, but mainly the value of its output voltage at resonance, given a standardized input voltage from the carrier generator V1. This method causes the incident magnetic field level in the diaper to vary as the diaper conductance varies. In order to keep the incident field level constant, a second control system could vary the tuned circuit input voltage to maintain a constant output voltage at resonance. As the diaper conductance increases, indicating increased excrement level, the controlled tuned circuit input level would also increase.

There may also be a need to vary the penetration distance of the probe induction field. This could be accomplished by significant changes of probe operating frequency; as higher frequencies provide larger penetration distances. By varying the operating/resonant frequency, excitation of conducting material and tissue internal and external to the body, such as within a diaper, can be selected. Measurement results shown in Teichmann et. al., "Sensors" Vol 14, 1039-1056, 2014, suggest that measurement depths vary from about 1 to 3 cm as the sensor probe operating frequency is varied from 5 MHz to 20 MHz. In addition to selecting the measurement depth, such frequency variation could be used for one dimensional image formation. Second and third dimensional image formation may be accomplished using multiple probes.

It should be understood that there are many types of circuits that detect the amount of magnetic field loss in an inductor, whether or not contained in a tuned circuit, in order to determine overall conductivity of nearby objects or media. The circuit employed in FIGS. 3 and 4 represent only one example.

Figure 5:
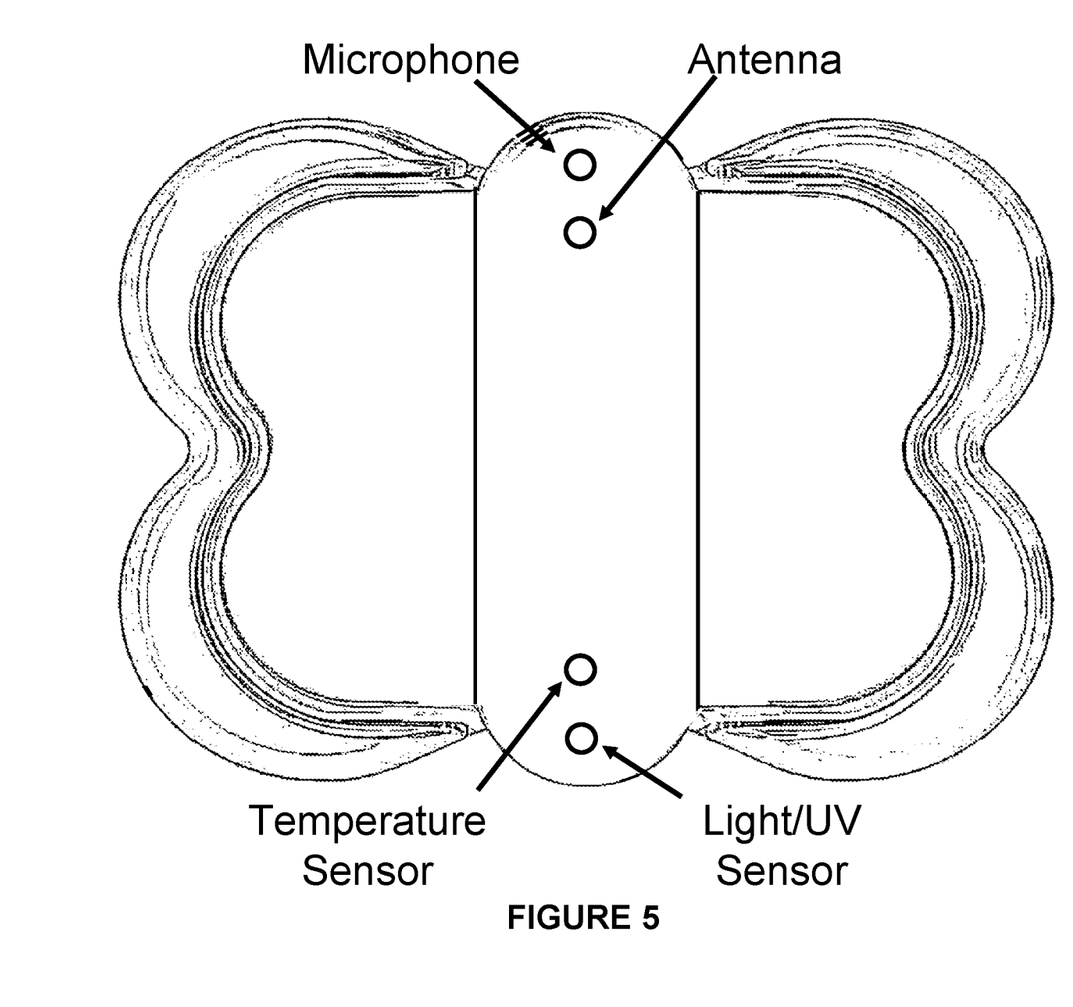
FIG. 5 shows the top side of said example instrument apparatus, showing example locations of sensors to gather data about internal conditions and external environment of the subject and communicate said data to caretakers and other interested parties.

Use of a multiplicity of sensors in order to improve the reliability of measurements is a key feature of the Subject invention. FIG. 5 also shows the butterfly shaped appliance containing measuring instruments and communication apparatus, as seen from the side that faces away from the Subject. Here, the attachment mechanism is shown closed in order to grasp the clothing (not shown). Also indicated is the region where the RF communications antenna may be located inside the enclosure. The Light/UV sensor could be located at one end of the "body", as an indicator of normal ambient light on the Subject, as well as damaging ultra-violet radiation. An additional sensor for infra-red radiation could also be added. At the other end of the butterfly "body" could be the microphone that monitors ambient sounds of the subject and others. Next to the Light/UV sensor could be an ambient temperature measuring sensor. For the light, temperature, and sound sensors, the Silicon enclosure could have modified properties to pass light and sound and temperature information but still maintain integrity such as water-proofing and safety.

Figure 6:
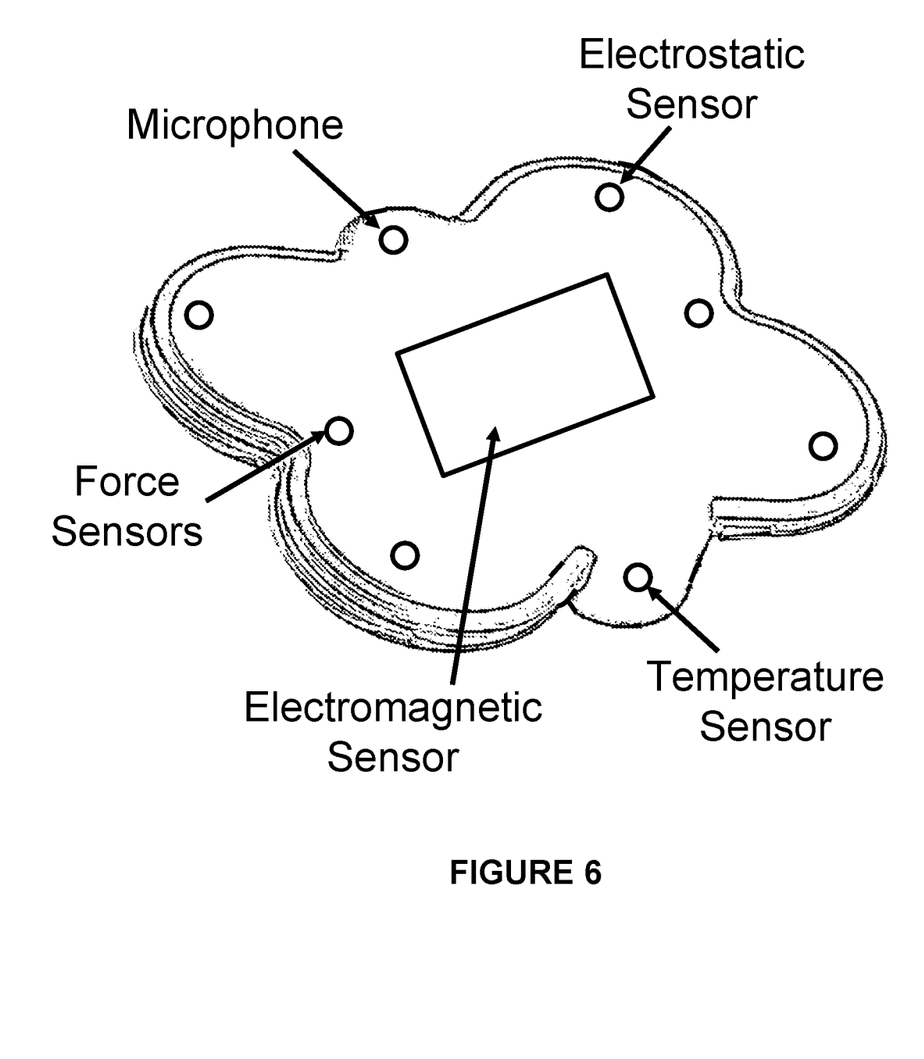
FIG. 6 shows the bottom side of said example instrument apparatus, showing additional example locations of sensors to gather data about internal conditions and external environment of the subject and communicate said data to caretakers and other interested parties.

FIG. 6 shows the side of the butterfly shaped appliance that faces the Subject. The microphone on this side picks up internal sounds from the Subject's body, and the temperature sensor picks up internal "core" body temperature. The electromagnetic and electrostatic sensors could pick up motion and properties of internal organs and fluids, in addition to conductivity of clothing related to wetness. The items marked "force sensors" are 3-axis accelerometers that also help determine motion of internal organs, but mainly sense motion and position of the body as a whole.

The different types of sensors, and multiple sets of sensors of the same type provide measurements of many bodily functions as well as provide additional accuracy, redundancy and reliability of said measurements. Although the magnetic sensor probe "Electromagnetic Sensor" is the primary means for detecting excrement in the diaper or other undergarment, several other sensors provide assistance for this task. Wholesale bodily motion, such as turning in one's sleep, can decrease reliability of the magnetic probe measurement, causing a "false positive" indication of excrement. Such bodily motion is detected by the accelerometers "Force Sensors", and magnetic sensor readings could be disregarded during this period of motion. The internally directed microphone can also sense the excretion bodily function while it is occurring. Excreta also cause temperature changes, detected by the internally directed temperature sensor. Operating together, the fusion of multiple sensor data reduces the probability of missing an event or reporting an event that has not occurred.

The details provided in the above description describe particular implementations of the systems for determining the presence of excrement within diapers and other undergarments. Other embodiments could be implemented in any other suitable manner. For example, the above description describes particular voltages, frequencies, gains, resistances, capacitances, currents, and other values. These values are for illustration only. Other embodiments could use different key system blocks, voltages, frequencies, levels, gains, resistances, capacitances, and other values depending on the implementation.

It may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus for contactless detection of solid or wet excrement within an underclothing, comprising
    an enclosure containing an alternating electric current source driving a first alternating current into a magnetic probe consisting of a coil inductor within a parallel tuned circuit that thereby creates a first static magnetic induction field,
    where the first magnetic induction field penetrates inward through all clothing and induces a second alternating electric current within the solid or wet excrement,
    where the second alternating electric current is sufficiently minute to prevent health risk to a wearer of the underclothing,
    wherein the second alternating electric current creates a second magnetic induction field that penetrates outward through said all clothing to reach the coil inductor,
    wherein the intensity of the first magnetic induction field is reduced based upon the quantity of the solid or wet excrement,
    whereby the enclosure can be handheld or attached to the outside of the underclothing or any other layer of clothing,
    thereby requiring no devices or equipment to be located inside or adjacent to the underclothing or within any other clothing and eliminating the need for the underclothing to be specially designed to accommodate operation of the apparatus.

2. The apparatus of claim 1, whereby additional sensors contained within the enclosure, including acceleration and electrostatic, are used along with the coil inductor magnetic probe to increase reliability of excrement detection in said underclothing.

3. The apparatus of claim 2, wherein said additional sensors also include those for sound and temperature.

* * * * *